US00PP31658P2

(12) United States Plant Patent
Werner

(10) Patent No.: US PP31,658 P2
(45) Date of Patent: Apr. 14, 2020

(54) ***CERCIS* PLANT NAMED 'NC2015-12'**

(50) Latin Name: *Cercis canadensis*
Varietal Denomination: NC2015-12

(71) Applicant: North Carolina State University, Raleigh, NC (US)

(72) Inventor: Dennis James Werner, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 0 days.

(21) Appl. No.: 16/350,672

(22) Filed: Dec. 19, 2018

(51) Int. Cl.
*A01H 6/00* (2018.01)
*A01H 5/02* (2018.01)

(52) U.S. Cl.
USPC ..... Plt./216

(58) Field of Classification Search
USPC ..... Plt./216
CPC ..... A01H 6/00; A01H 5/02
See application file for complete search history.

(56) References Cited

U.S. PATENT DOCUMENTS

PP10,328 P 4/1998 Covey
PP17,740 P3 5/2007 Roethling

OTHER PUBLICATIONS

Roberts et al (Horticulture Research, vol. 2, No. 15049, 2015).*

* cited by examiner

*Primary Examiner* — Keith O. Robinson
(74) *Attorney, Agent, or Firm* — Buchanan Ingersoll & Rooney PC

(57) ABSTRACT

A new and distinct variety of *Cercis canadensis* eastern redbud plant, herein referred to by its cultivar name, 'NC2015-12', is provided which forms gold colored foliage. The new variety provides vegetation that is moderately vigorous and the growth habit is weeping. The new variety is well suited for providing attractive ornamentation in the landscape.

2 Drawing Sheets

Botanical/commercial classification:
Latin name—*Cercis canadensis.*
Common name—eastern redbud.
Varietal denomination: 'NC2015-12'.

SUMMARY OF THE INVENTION

The new variety of *Cercis canadensis* eastern redbud plant was created in a controlled breeding program during March, 2009 at Raleigh, N.C., U.S.A., by a controlled cross wherein two parents were crossed which previously had been studied in the hope that they would contribute the desired characteristics. The female parent (i.e., the seed parent) was the 'Covey' variety (U.S. Plant Pat. No. 10,328). The male parent (i.e., the pollen parent) was the 'Hearts of Gold' variety (U.S. Plant Pat. No. 17,740).

The parentage of the new variety can be summarized as follows:

'Covey' x 'Hearts of Gold'

The new cultivar was discovered and selected as a single seedling within the second generation progeny of the above-stated open-pollination at Jackson Springs, N.C. Selective study resulted in the identification of a single plant of the new variety in 2015.

It was found that the new variety of *Cercis* plant of the present invention possesses the following combination of characteristics:

(a) forms attractive, gold colored foliage,
(b) exhibits weeping growth habit; and
(c) provides moderately vigorous vegetation.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'Covey' variety (i.e., the seed parent) displays medium green colored foliage and the 'Hearts of Gold' variety (i.e., the pollen parent) displays upright vase shaped growth habit, whereas the new variety displays gold colored foliage and weeping growth habit. Moreover, the new variety can be readily distinguished from other similar non-parental varieties. For example, the 'Ruby Falls' variety (U.S. Plant Pat. No. 22,097) displays purple to burgundy colored foliage, whereas the new variety displays gold colored foliage.

The new variety has been found to undergo asexual propagation at Belvidere, Tenn. by chip budding since 2015. Asexual propagation by chip budding in Belvidere, Tenn. has shown that the characteristics of the new variety are stable and are strictly transmissible by such asexual propagation from one generation to another. Accordingly, the new variety undergoes asexual propagation in a true-to-type manner.

BRIEF DESCRIPTION OF THE PHOTOGRAPHS

The accompanying photographs shows as nearly true as it is reasonably possible to make the same, in color illustrations of this character, typical specimens of the new variety.

The *Cercis* plants of the new variety were approximately two years of age and were observed at the beginning of the third growing season at Jackson Spring, N.C., U.S.A. while growing outdoors.

Figure 1:
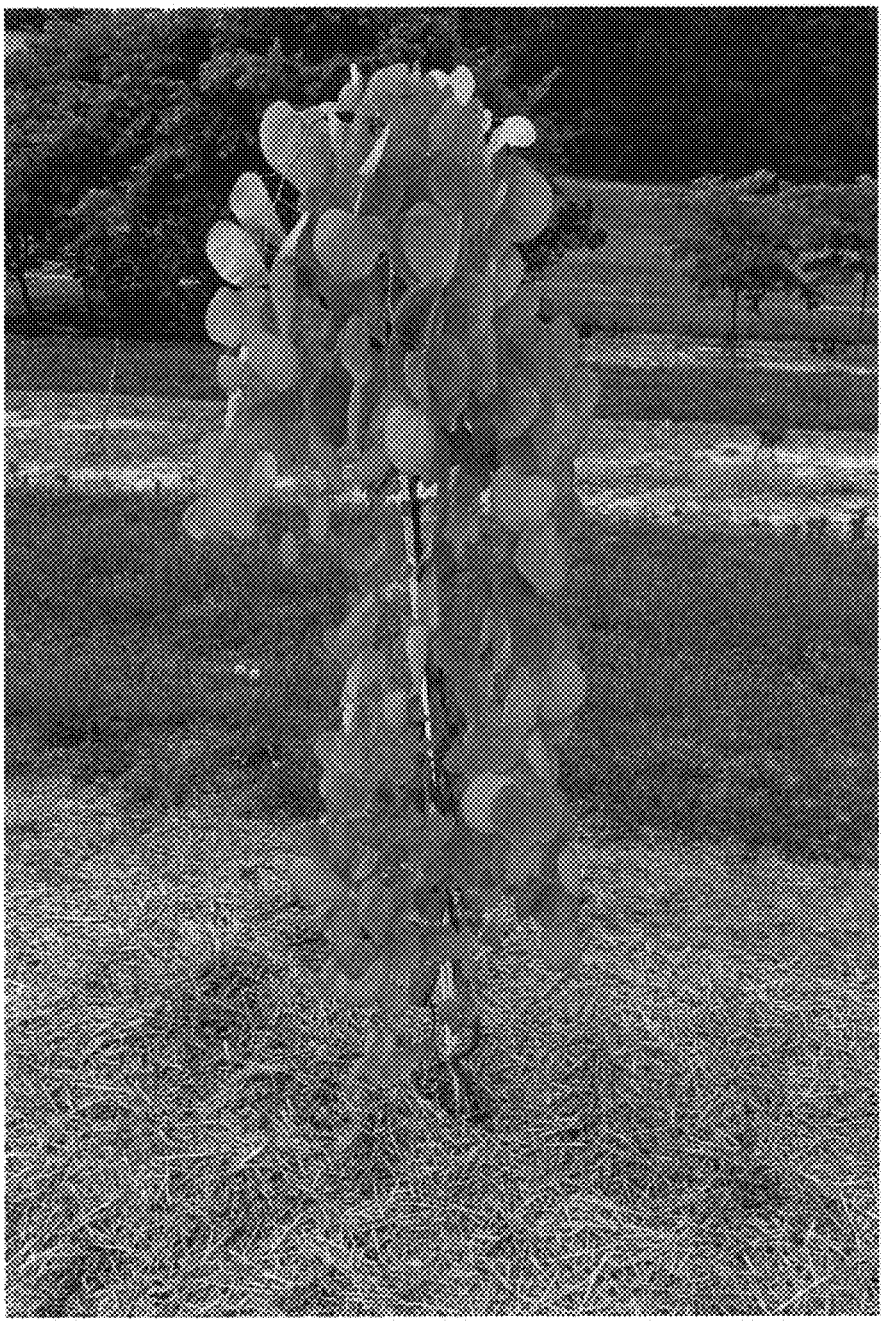

FIG. 1—illustrates a specimen the tree—side view.

Figure 2:
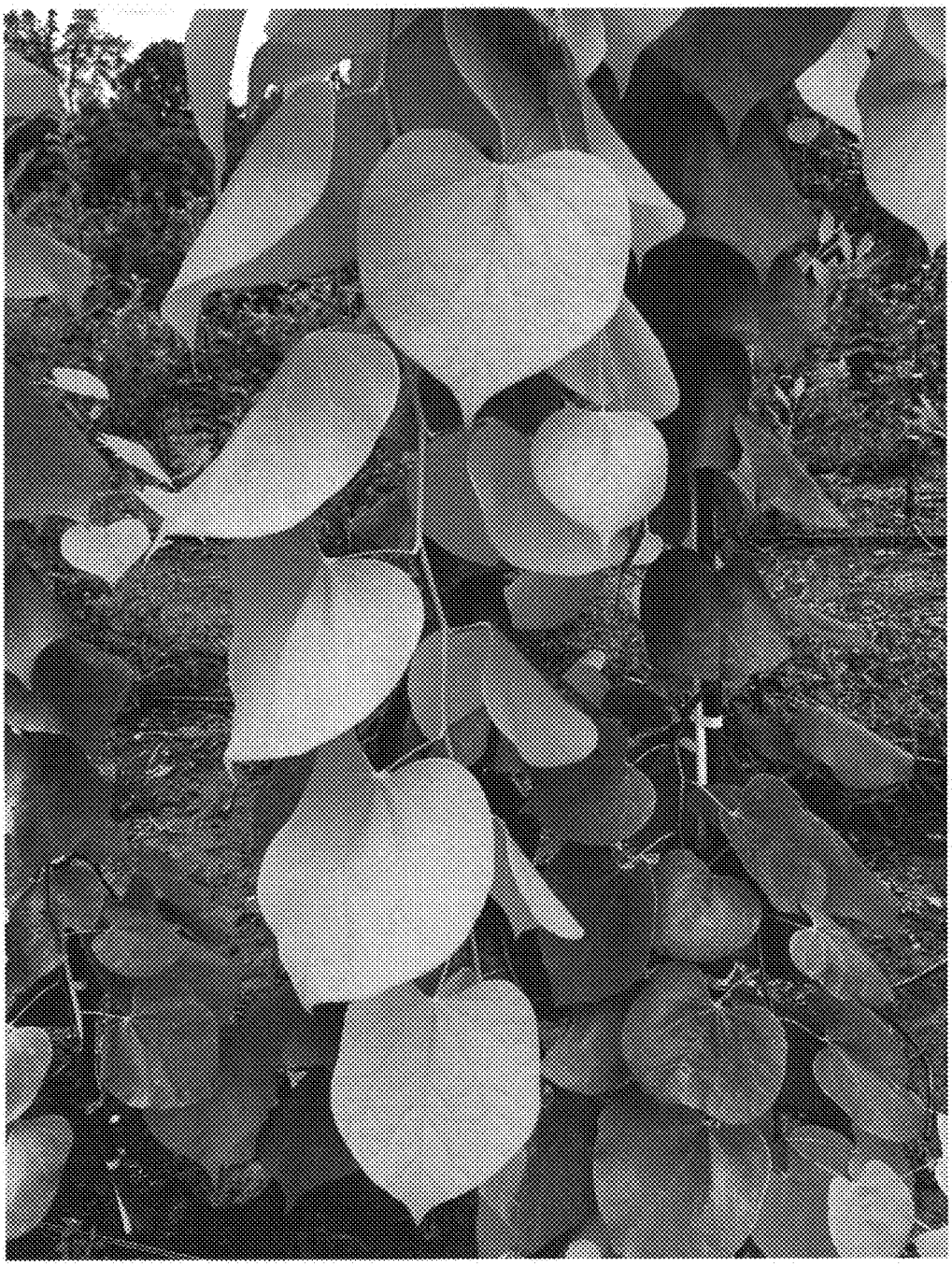

FIG. 2—illustrates a specimen of the foliage—close view.

DETAILED BOTANICAL DESCRIPTION

The chart used in the identification of colors described herein is The Royal Horticultural Society ("R.H.S." Colour Chart), London, England, 2015 edition. The terminology which precedes reference to the chart has been added to indicate the corresponding color in more common terms. The color values of the flowers were determined in April 2019 and the color values of the foliage were determined in June 2019 under natural light conditions in Cochranville, Pa.

The following descriptions and measurements describe plants produced from chip budding and grown outside in a test field in Cochranville, Pa. Plants were approximately three years of age. Measurements and numerical values represent averages of typical plants.

Class: *Cercis* Plant.

Plant:

*Growth habit*.—Weeping.

*Type*.—Deciduous perennial tree.

*General appearance*.—Moderately vigorous.

*Size*.—Height: approximately 1.9 meters. — width: approximately 70 cm.

*Trunk*.—Diameter immediately above graft union: approximately 2.5 cm. — texture: slightly rugose.

*Branches*.—Generally: highly branched and weeping. — strength: moderately strong. — diameter of new growth: approximately 2.0 mm. — diameter of one-year old growth: approximately 9.0 mm. — texture of new growth: glabrous. — color of young stem: commonly near Grey-Brown Group N199A. — color of mature stem: commonly near Greyed-Green Group 197A. — lenticel: numerous, tiny; length is less than 1.0 mm on average; shape is elliptic; color is commonly near Grey-Brown Group N199D.

Foliage:

*General description*.—Type: deciduous. — arrangement: alternate.

*Leaves*.—Shape: cordate. — apex: acute. — base: cordate. — margin: entire. — length: approximately 7.5 cm. — width: approximately 9.5 cm. — texture of upper and lower surfaces: smooth, glabrous. — venation pattern: palmate. — color of upper and lower surfaces of young foliage: commonly near Greyed-Orange Group 164A and near Greyed-Orange Group 165C with venation of near Yellow-Green Group 145B. — color of upper surface of mature foliage: commonly near Yellow-Green Group N144C with venation of commonly near Yellow-Green Group N144D. — color of lower surface of mature foliage: commonly near Green Group 142C with venation of commonly near Green Group 142D. — fragrance: none detected.

*Petiole*.—Length: approximately 4.0 cm. — diameter: approximately 1.1 mm. — texture: smooth, glabrous. — color: commonly near Greyed-Orange Group 165B.

Flowering description:

*Flowering season*.—Flowers in early spring.

*General description*.—Compound corymbs. — aspect: facing upward to slightly outward. — fragrance: none noticeable. — quantity per plant: approximately 150-180. — diameter: approximately 4.0 cm to 10.0 cm. — height: approximately 2.0 cm.

*Peduncle*.—Strength: strong. — shape: rounded. — aspect: erect to about 45° from branch axis. — length: approximately 1.0 cm. — diameter: approximately 0.2 cm. — texture: glabrous. — color: commonly near Greyed-Purple Group 185D.

Flower description:

*General description*.—Type: single, rotate, not persistent. — aspect: upright. — quantity per inflorescence: approximately 9 per cluster.

*Bud just before opening*.—Shape: ovate tapering to a point. — diameter: approximately 3.0 mm. — length: approximately 7.0 mm. — color: commonly near Greyed-Purple Group 186A on the lower bud and near Greyed-Purple Group 186C on the top of the bud. — texture: glabrous.

*Corolla*.—Diameter: approximately 1.0 cm. — depth: approximately 1.0 cm.

*Petals*.—Quantity: 5, unfused. — shape: orbicular. — margin: entire. — apex: rounded. — base: obtuse. — length: approximately 9.0 mm. — width: approximately 4.0 mm. — texture of upper and lower surfaces: glabrous. — color of upper and lower surfaces when first and fully open: upper two petals have blotches of commonly near Red-Purple Group N74C over Red-Purple Group N74D on outer surface; inner surface is commonly near Red-Purple NN74C. Lower two petals are commonly near Purple Group 77D.

*Calyx*.—Shape: vase-shaped; 5 rounded lobes at terminus. — diameter: approximately 6.0 mm at top of hypanthium. — length: approximately 5.0 mm. — color of outer and inner surfaces: commonly near Red-Purple Group 59C fading to near Red-Purple Group 59B at base. — texture of inner and outer surfaces: glabrous.

*Sepals*.—Quantity: 5, attached to top of hypanthium. — arrangement: in a single whorl.

*Pedicel*.—Strength: strong. — shape: round. — length: approximately 1.0 cm. — diameter: less than 1.0 mm. — texture: glabrous. — color: commonly near Greyed-Purple Group 185D.

*Reproductive organs*.—Androecium: — Stamen quantity per flower: 10 on average, unfused and attached to apex of hypanthium. — Stamen length: approximately 9.0 mm. — Filament: length is approximately 8.0 mm; color is commonly near Greyed-Purple Group 186D. — Anther: shape is round to slightly oblong; length is less than 1.0 mm; width is less than 1.0 mm; color is commonly near Greyed-Red Group 181B to Brown Group 200B. — Pollen: amount is abundant; color is commonly near Greyed-Yellow Group 161D. — Gynoecium: — Pistil: quantity is 1 per flower; length is approximately 7.0 mm on average; width is less than 1.0 mm; color is commonly near Yellow-Green Group 144A; texture is glabrous. — Stigma: shape is round; color is commonly near Greyed-Yellow Group 161D; length is less than 1.0 mm; width is less than 1.0 mm. — Style: shape is elongate; width is less than 1.0 mm; color is commonly near Greyed-Purple Group 186A towards the apex and near Yellow-Green Group 144A at the base. — Ovary: position is superior; shape is round; width is less than 1.0 mm; color is commonly near Yellow-Green Group 144A.

*Seed production*.—None observed to date.

Development:

*Vegetation*.—Moderately vigorous.

*Disease and pest resistance*.—Plants of the new variety have not been noted to be resistant to pathogens and pests common to *Cercis* plants.

*Commercial crop time*.—Approximately 1.5 years from budding to finish as a 4 to 6-foot tree.

The new 'NC2015-12' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of *Cercis* plant characterized by the following combination of characteristics:

(a) forms attractive, gold colored foliage, (b) exhibits weeping growth habit; and (c) provides moderately vigorous vegetation;

substantially as herein shown and described.

* * * * *